(12) United States Patent
Tornero Garcia et al.

(10) Patent No.: US 12,324,861 B2
(45) Date of Patent: Jun. 10, 2025

(54) BEADED NONWOVEN MEMBRANE AS A DRUG DELIVERY SYSTEM

(71) Applicant: CEBIOTEX, S.L., Barcelona (ES)

(72) Inventors: Jose Antonio Tornero Garcia, Viladecavalls (ES); Francesc Cano Casas, Terrassa (ES); Luc Michelguy Marti Clausez, Barcelona (ES); Joan Bertran Llavina, Arenys de Mar (ES)

(73) Assignee: CEBIOTEX, S.L., Barcelona (ES)

( * ) Notice: Subject to any disclaimer, the term of this patent is extended or adjusted under 35 U.S.C. 154(b) by 184 days.

(21) Appl. No.: 17/263,115

(22) PCT Filed: Aug. 2, 2019

(86) PCT No.: PCT/EP2019/070887
§ 371 (c)(1),
(2) Date: Jan. 25, 2021

(87) PCT Pub. No.: WO2020/025793
PCT Pub. Date: Feb. 6, 2020

(65) Prior Publication Data
US 2021/0154151 A1    May 27, 2021

(30) Foreign Application Priority Data

Aug. 3, 2018  (EP) .................................... 18382589

(51) Int. Cl.
| | | |
|---|---|---|
| *A61K 9/00* | (2006.01) | |
| *A61K 9/14* | (2006.01) | |
| *A61K 9/70* | (2006.01) | |
| *A61K 31/4745* | (2006.01) | |
| *D04H 1/435* | (2012.01) | |
| *D04H 1/728* | (2012.01) | |

(52) U.S. Cl.
CPC ............ *A61K 9/7007* (2013.01); *A61K 9/146* (2013.01); *A61K 31/4745* (2013.01); *D04H 1/435* (2013.01); *D04H 1/728* (2013.01)

(58) Field of Classification Search
None
See application file for complete search history.

(56) References Cited

U.S. PATENT DOCUMENTS

| | | |
|---|---|---|
| 2005/0158362 A1 | 7/2005 | Wheatley et al. |
| 2018/0000744 A1 | 1/2018 | Khan et al. |

FOREIGN PATENT DOCUMENTS

| | | |
|---|---|---|
| CN | 103599090 A | 2/2014 |
| CN | 105386155 A | 3/2016 |
| CN | 106727447 A | 5/2017 |

(Continued)

OTHER PUBLICATIONS

International Search Report mailed Oct. 29, 2019 for International Application No. PCT/EP2019/070887, 4 pages, English translation.

(Continued)

*Primary Examiner* — Paul W Dickinson
(74) *Attorney, Agent, or Firm* — Squire Patton Boggs (US) LLP

(57) ABSTRACT

It relates to a beaded nonwoven membrane comprising polymeric nanofibers and at least one active agent, wherein the active agent has a water solubility equal to or lower than 33 mg/mL. It also relates to a process for the preparation of the beaded nonwoven membrane, and to its use in medical, and veterinary applications.

19 Claims, 7 Drawing Sheets

(56) References Cited

FOREIGN PATENT DOCUMENTS

| CN | 107675364 A | 2/2018 |
|---|---|---|
| JP | 2012-219384 A | 11/2012 |
| WO | WO 2013/144206 A1 | 10/2013 |

OTHER PUBLICATIONS

Written Opinion of the International Searching Authority mailed Oct. 29, 2019 for International Application No. PCT/EP2019/070887, 8 pages, English translation.
International Preliminary Report on Patentability mailed Apr. 8, 2020 for International Application No. PCT/EP2019/070887, 21 pages, English translation.
Balaji, et al: "An insight on electrospun nanofibers inspired modern drug delivery system in the treatment of dreadful cancers", Royal Society of Chemistry; Jan. 1, 2015, pp. 57984-58004.
Ramakrishna, et al: "Advances in drug delivery via electrospun and electrosprayed nanomaterials", International Journal of Nanomedicine 2013; vol. 8, pp. 2997-3017.
Beads Formation in Electrospinning http://electrospin.com/beads.html#.Y3YSBuTMKU1; two pages.
Fong, et al: "Beaded nanofibers formed during electrospinning", Polymer 1999; vol. 40, pp. 4585-4592.
Falde, et al: "Layered Superhydrophobic Meshes for Controlled Drug Release", J Control Release; Sep. 28, 2015; vol. 214(23); pp. 23-29.

BEADED NONWOVEN MEMBRANE AS A DRUG DELIVERY SYSTEM

CROSS-REFERENCE

This application is a 35 USC 371 national phase filing of PCT/EP2019/070887 filed on Aug. 2, 2019, which claims the benefit of and priority to European Patent Application EP18382589.2 filed on Aug. 3, 2018, both applications are incorporated herein by reference in their entirety.

This application claims the benefit of European Patent Application EP18382589.2 filed on Aug. 3, 2018.

TECHNICAL FIELD

The present invention generally relates to the field of drug delivery systems (DDS). More particularly, it relates to a beaded nonwoven membrane for the controlled and sustained release of active agents of limited water solubility to an area of the body to be treated. It also relates to a process for the preparation of the beaded nonwoven membrane, and to its use in medical and veterinary applications.

BACKGROUND ART

Treatment of most malignant solid tumors relies on a combination of local control (surgery and radiation therapy; RT) and systemic chemotherapy. Local tumor recurrence after resection surgery and RT remains a challenge. Despite local control of high-risk neuroblastoma, local tumor recurrences are developed in 10% of newly diagnosed patients and 50% of patients with locally persistent re-resected disease. Incidence of local recurrence after first complete remission in other malignancies cancer such as Soft Tissue Sarcomas, Glioblastoma, Pancreas and primary localized rhabdomyosarcoma is high. The relevance of an adequate local control is underscored by the worse outcome observed in patients that develop local failure after initial complete remission. The intensification of RT to improve local control after resection surgery is limited by unacceptable toxicity, especially in young children, and the increased risk of second malignancies. In this context, new technology platforms are urgently called for to overcome the drawbacks associated with RT after tumor resection especially in children.

SN-38 (10-hydroxy-campthothecin) in its lactone (active) form is a poorly soluble molecule that has shown potent preclinical activity against several pediatric solid tumors. Irinotecan, the marketed soluble prodrug of SN-38, undergoes extensive conversion (>70%) to SN-38 in nude mice, though it has demonstrated low clinical efficacy, likely due to only partial conversion (less than 10%) into the active derivative upon systemic administration in patients. In addition, SN-38 is rapidly hydrolyzed to an inactive carboxylate form in plasma. In addition to its instability at physiological pH, the delivery of SN-38 also faces the challenge of its toxicity in the body.

Many attempts have been made to increase the solubility of SN-38, stabilize the lactone ring, and mitigate its toxicity. For example, physical methods such as nanoparticle encapsulation, cyclodextrin complexation; chemical methods such as prodrugs, polymer-, albumin- and immunoconjugates; and enzyme activated prodrug therapy have been developed. However, these strategies have yielded only limited success.

Polymeric drug delivery systems (DDSs) for the localized delivery of anticancer drugs emerged as one of the most promising approaches to treat resectable solid tumors. DDSs can be classified according to the mechanism that controls the release of the drug, such as diffusion-controlled systems, chemically controlled systems, solvent-activated systems, modulated-release systems and bioerodible-release systems. Bioerodible controlled release systems have the advantage over other release systems in that there is no need to surgically remove the drug depleted device. Besides, advantages of localized delivery comprise reduced systemic exposure to highly toxic agents and achievement of high local concentration of potent anticancer agents that are not suitable for systemic administration due to poor aqueous solubility. However, the lack of comprehensive preclinical studies aiming to understand the pharmacokinetics of localized DDS in cancer still represents a significant hurdle towards a robust bench-to-bedside translation.

Electrospun polymer nanofiber matrices appear as one of the most versatile, reproducible and scalable nano-DDS. They allow adjusting their size and shape to fill the space left by tumor resection, and provide a large surface area and porosity that facilitate the efficient release of the active cargo from the DDS to the tumor tissue. Moreover, their monolithic nature eases manipulation, implantation and retention in the action body site, and prevents the characteristic migration of nanoparticles and microparticles.

The PCT application WO2013144206 discloses a nonwoven membrane comprising biocompatible electrospun nanofibers and at least one active agent having water solubility lower than 33 mg/mL, which is entangled between the nanofibers. The nonwoven membrane disclosed in this document is able to release the active agent once the latter is solubilized.

Nonwoven membranes prepared by electrospinning may shrink under physiological conditions. Several strategies have been proposed to reduce shrinkage of nonwoven mats. For example, some strategies consist in using combinations of polymers in the electrospinning process. However, the introduction of further polymers in the membranes may be detrimental for the biodegradation of the drug delivery system, and, in general, it makes the preparation process more tedious and difficult. In this regard, the use of a mixture of different polymers makes it difficult to obtain a membrane with a reproducible composition between batches and reduces the number of suitable solvents, which compromises the robustness and the reproducibility of the electrospinning process. Another strategy to reduce the shrinkage of the membrane involves the treatment of the membrane after its production, but this requires sinking it in water, which would trigger the release of its active content, therefore making it unfeasible for the production of drug delivery membranes.

US2018000744 discloses core/shell nanomaterials wherein the active agent is in the core component, more particularly it is encapsulated in a biodegradable polymer. These nanomaterials are obtained by coaxial electrospinning. Coaxial electrospinning is reported e.g. by Seeram Ramakrishna in International Journal of Nanomedicine 2013, page 2997. CN105386155 discloses beaded nanofibers wherein the active agent is placed inside the beads. The beads are used to improve drug loading rate. The nanofibers are prepared by electrospinning of a mixture of polymer and active agent. CN107675364 discloses dual drug-loaded fiber membranes with a filament-beading structure which are prepared by electrospinning, wherein the drug is encapsulated in micron-sized beads. CN106727447 discloses a beaded nanofibrous membrane which contains an antineoplastic drug inside the fibers. The nanofibers are prepared by electrospinning of a mixture of polymer and active agent. A drawback of all these prior art membranes is that they do not allow a reproducible, efficient, and complete sustained release in particular within a few days after initial contact with the delivery medium. Besides, these documents are silent with respect to the shrinkage behaviour of the membranes.

Therefore, there is a need to develop drug delivery systems for the controlled and sustained release of active agents in biomedical applications that overcome the problems of the state of the art.

SUMMARY OF INVENTION

The inventors have developed a new stable drug delivery system in the form of a beaded nonwoven membrane that is able to locally release active agents of limited solubility to an area to be treated in a controlled and sustained manner.

The inventors have surprisingly found that the presence of beads in the nonwoven membrane significantly reduces shrinkage of an analogous bead-free nonwoven membrane. The nonwoven membrane of the invention having beaded morphology shows dimensional stability, i.e., it does not show significant shrinkage once it is placed into the body under physiological conditions. In particular, as can be seen in the examples herein, the linear shrinkage of the membrane of the invention was reduced more than 50% with respect to an analogous bead-free membrane disclosed in the PCT application WO2013144206.

Generally speaking, it is desired to reduce shrinkage of such delivery systems for many medical and biological applications. Membranes showing having a low degree of shrinkage are more suitable to be implanted because they do not show any significant change in geometry and flexibility.

In addition, the less the membrane shrinks, the lower the mass per unit area is. As a consequence, the rigidity of the membrane is reduced, which may avoid producing lesions in the area where it is implanted, and the membrane has an improved drapability e.g. to the organ or surgical site when the delivery agent is a therapeutic agent. Furthermore, the beaded nonwoven membrane of the invention has smooth touch and is easier to manipulate.

Additionally, in case of lower shrinkage, the spaces between the nanofibers, through which the drug in it solubilized form may be released, are less reduced such that the drug release is not hindered and the release profile is not adversely affected.

Advantageously, due to the reduced shrinkage, the nonwoven membrane of the invention, which is cut in dry state to cover a specific surface to be treated, will cover almost all the surface to be treated when it is in wet state; while high-shrinkage membranes (cut in dry state) would reduce noticeably their size when it is in wet state, thus leaving a major area that should be treated uncovered. This means that e.g. a surgeon who wants to cover a specific body area with the beaded membrane of the invention will need to cut a piece of membrane which is only slightly larger than the area to be treated, whereas when a bead-free membrane is used, given the unpredictable shrinking degree, a much larger piece of membrane is needed to cover the same area, and still until application of the membrane in the area to be treated it will not be known if it was enough to cover it.

The presence of beads in a nonwoven membrane to be used as a drug delivery system is usually not an option to consider for an expert skilled in the art. Rather, the bead formation is mostly prevented because the operating range of the preparation process (e.g. electrospinning) is generally reduced. Nevertheless, the inventors have found an appropriate process to produce the desired beads having the advantages mentioned above.

Therefore, a first aspect of the invention relates to a beaded nonwoven membrane comprising polymeric nanofibers, and at least one active agent, wherein:
  the nanofibers comprise beads distributed along the nanofiber length and have a mean diameter which is from 1.5 to 20 times the mean diameter of the nanofiber,
  the active agent has a water solubility equal to or lower than 33 mg/mL, and
  the total content of the active agent is physically entrapped within the membrane but externally arranged to the polymeric nanofibers of the membrane.

The nonwoven membrane as previously defined having beaded morphology may be prepared by an electrospinning process. Thus, a second aspect of the invention relates to a process for the preparation of the beaded nonwoven membrane as previously defined, which comprises the following steps:
  a) preparing a solution of one or more polymers in a suitable solvent system,
  b) preparing a solution or a suspension of the active agent in a suitable solvent system, particularly wherein the polymer or polymers from step a) are insoluble;
  c) carrying out the electrospinning of the solution from step a) to produce beaded polymeric nanofibers, and, simultaneously, depositing the solution or suspension of step b) over the polymeric nanofibers; and
  d) optionally, drying the nonwoven membrane obtained from step c).

The beaded nonwoven membrane of the present invention may be used as a drug delivery system (DDS) for the treatment of diseases. Thus, a third aspect of the invention relates to a beaded nonwoven membrane as previously defined for use as a medicament. When the active agent contained in the beaded nonwoven membrane of the invention is a chemotherapeutic agent, it can be used in the treatment of tumors. Accordingly, another aspect of the invention relates to the beaded nonwoven membrane as previously defined which comprises a chemotherapeutic agent for use in the treatment of tumors.

BRIEF DESCRIPTION OF DRAWINGS

FIG. 8 shows a scanning electron micrograph of a beaded nonwoven membrane analog to example 1 but further comprising a surfactant, at 500× magnifications (FIG. 8A) and 3000× magnifications (FIG. 8B, wherein B: beads, F: fibers, and A: SN-38 crystals).

DETAILED DESCRIPTION OF THE INVENTION

Figure 1A:
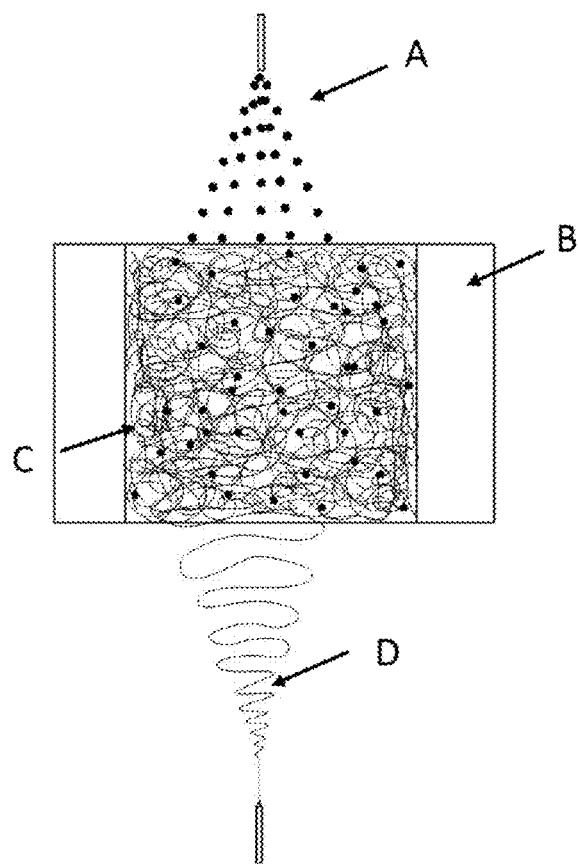
FIG. 1 shows different techniques for the deposition of the active agent in the membrane while nanofibers are produced: on a rotating cylindrical collector either along the horizontal axis (see FIG. 1A; A: API spray/dispensing, B: Rotating collector, C: Formation of membrane, D: Electrospinning of fibers), or the vertical axis (see FIG. 1B; A: API spray/dispensing, B: Rotating collector vertical axis, C: Formation of membrane, D: Electrospinning of fibers); on a static collector by moving fibre and active agent pouring devices (FIG. 1C; A: API spray/dispensing (moving), B: Static collector, C: Formation of membrane, D: Electrospinning of fibers (moving)); and in the inner surface of a rotating collector (FIG. 1D; A: API spray/dispensing, B: Rotating collector, C: Formation of membrane, D: Electrospinning of fibers).
Figure 1B:
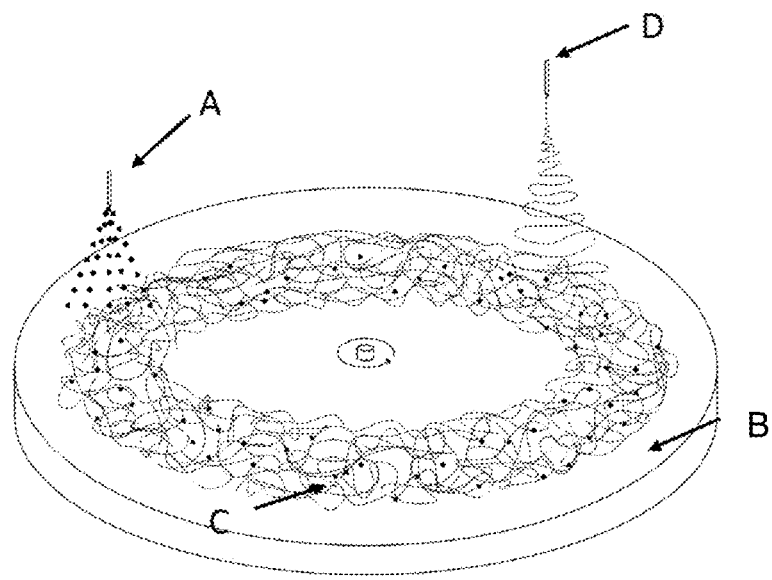

All terms as used herein in this application, unless otherwise stated, shall be understood in their ordinary meaning as known in the art. Other more specific definitions for certain terms as used in the present application are as described below and are intended to apply uniformly through-out the specification and claims.

The term "about" or "around" as used herein refers to a range of values ±10% of a specified value. For example, the expression "about 10" or "around 10" includes ±10% of 10, i.e. from 9 to 11.

The present invention relates to a beaded nonwoven membrane comprising polymeric nanofibers and an active agent. In the context of the invention, the term "nonwoven membrane" relates to a porous sheet (film) of arbitrarily-deposited polymeric nanofibers on a solid surface (collector) and optionally entangled by one or more of following methods: physical methods such as adhesion with a biocompatible glue, melting or solvent excess and mechanical methods such as needle punching and the interlacing by water or pneumatic injectors. The membrane fibres may or may not be interconnected; they may be cut or continuous fibres and may comprise only one material or different materials, either as a combination of different fibres or as a combination of similar fibres of different materials. These different configurations can be arranged in the same membrane in different layers during the production process.

The term "beaded nonwoven membrane" as used herein means that the nanofibers of the membrane show beads distributed along the nanofiber length thereby creating a nanofiber with beads-on-a-string (BOA) or "bead-and-string" morphology. All these terms may be used interchangeably. Typically, a "bead" refers to a nodulous part having a thickness equal to or more than 2 times the mean fibre diameter. The beaded morphology can be observed using Scanning Electron Microscope (SEM) micrographs. Beads usually are of short length (from 0.5 to 20 times their own diameter) and their cross section is circular. Their spacing along the nanofibers can be in a very wide range (this means that the distance between beads can be very diverse). A way to quantify the beads in a membrane is to provide the surface count per square $mm^2$ that can be observed by SEM in the external surface of the membrane, when a significant sampling is used. This count can be e.g. within a range from 1 to 10000 beads/$mm^2$.

The term "bead-free nonwoven membrane" as used herein means that the nanofibers of the membrane do not show any beads. i.e. a non-beaded membrane.

For the purposes of the invention, shrinkage, shrinking, degree of shrinkage, or synonyms always refer to linear shrinkage. The term "linear shrinkage" means a decrease in a single dimension of a nonwoven membrane comprising polymeric nanofibers when it is in wet state, i.e. it is contacted with a solubilizing medium (e.g. it is placed into the body under physiological conditions). The linear shrinkage is expressed as a percentage with respect to the original dimension and can be measured by cutting a membrane sample (e.g. 30×30 mm) in dry state, marking two pairs of points (e.g. separated 20 mm each), in longitudinal and cross section on the membranes (see FIG. 6), immersing the sample in a solvent (e.g. water at constant temperature (37.0° C.)), thereby obtaining the membrane in a wet state, and measuring the distance between the points of each sample (height and width) with a physical measurement tool like a caliper at a fixed time (e.g. at 24 h, 48 h and 72 h). The linear shrinkage in percentage is calculated by dividing the distance between the marked points in the membrane in wet state (i.e. after having contacted the membrane with a solubilizing agent), the analog distance between the marked points in the membrane in dry state and expressing the result as a percentage.

As used herein, the term "dry state" refers to a non-woven membrane which after its preparation has not been contacted with a solubilizing agent able to solubilize the active agent. By contrast, the term "wet state" refers to the state in which the non-woven membrane has been contacted with a solubilizing agent able to solubilize the active agent.

In one embodiment, optionally in combination with one or more features of the various embodiments described above or below throughout all the description, the solubilizing agent capable of solubilizing the active agent comprises water. The solubilizing agent may be any biological fluid, such as blood plasma, serum, extracellular fluid, limfatic fluid, encephaloraquidic fluid and the like.

In another particular embodiment, optionally in combination with one or more features of the various embodiments described above or below, the beads of the beaded nonwoven membrane have mean diameter from 2 to 25 μm, more particularly from 5 to 25 μm.

Typically, the mean diameters of the beads may be measured directly from by using scanning electron microscopy (SEM) images using ImageJ software. Usually several measurements of different parts of the membrane are performed.

Generally, a certain number of beads is desired in the beaded membrane of the invention. On the one hand, when the number of beads is too low, the membrane does not show an appropriate shrinkage reduction with respect to an analog bead-free membrane. On the other hand, when the number of beads is too high, then the resistance of the membrane is affected, since the nanofibers provide resistance to the membrane. Thus, in one particular embodiment, optionally in combination with one or more features of the various embodiments described above or below, the amount of beads of the beaded nonwoven membrane is from 500 to 5000, more particularly from 1000 to 2000 beads/mm$^2$.

Beads are measured by counting the number of beads in a SEM image of known dimensions and extrapolating at 1 mm$^2$. This is repeated with several SEM images in order to have values which are representative for the whole membrane.

The expression that "the total content of the active agent is physically entrapped within the membrane but externally arranged to the polymeric nanofibers of the membrane" means that the active agent is physically retained within the membrane (i.e. due to its size; because the active agent particles are larger than the spaces between the nanofibers, or because they have to physically cross the barrier of nanofibers to go outside of the membrane: the nanofibers act as a filter entrapping the particles) such that the active agent can only be released when is contacted with an appropriate amount of medium in which it is solubilized. Thus, in the beaded membrane of the invention, no active agent is placed inside or forms part of the polymeric nanofibers. Rather, substantially all the surface of the active agent is exposed to the medium. This configuration of the membrane results from the process used for its preparation in which the active agent is deposited on the nanofibers once they have been already formed. The term "substantially absent" as used herein refers to a surface equal to or higher than about 90%, 95% or 100% with respect to the total surface.

As a consequence, the beaded nonwoven membrane wherein the total content of the active agent is physically entrapped within the membrane but externally arranged to the polymeric nanofibers releases the active agent in the presence of a suitable medium (e.g. the physiological medium) only through solubilization and not by degradation of the polymeric nanofibers, unlike what occurs with membranes obtained by the electrospinning of a mixture of both, the polymer and active agent, wherein the active agent is necessarily partially or totally placed within the nanofibers. As shown in the examples, the beaded membranes of the invention allow a reproducible efficient and sustained release.

In particular, the membrane of the invention is capable to release a very significant amount of active agent from the first minutes and within a few days after initial contact with the delivery medium, and, afterwards, the release remains constant at a slower rate for a longer period of time until the total amount of active agent present is the membrane is released. This is desirable in certain applications, e.g. in oncology, where an important release is needed in the first hours after surgery.

Thus, the beaded membranes of the invention are able to completely release high therapeutic doses from the first minutes and during days or weeks at therapeutics doses and well before the polymeric nanofibers of the membrane are degraded.

Figure 10:
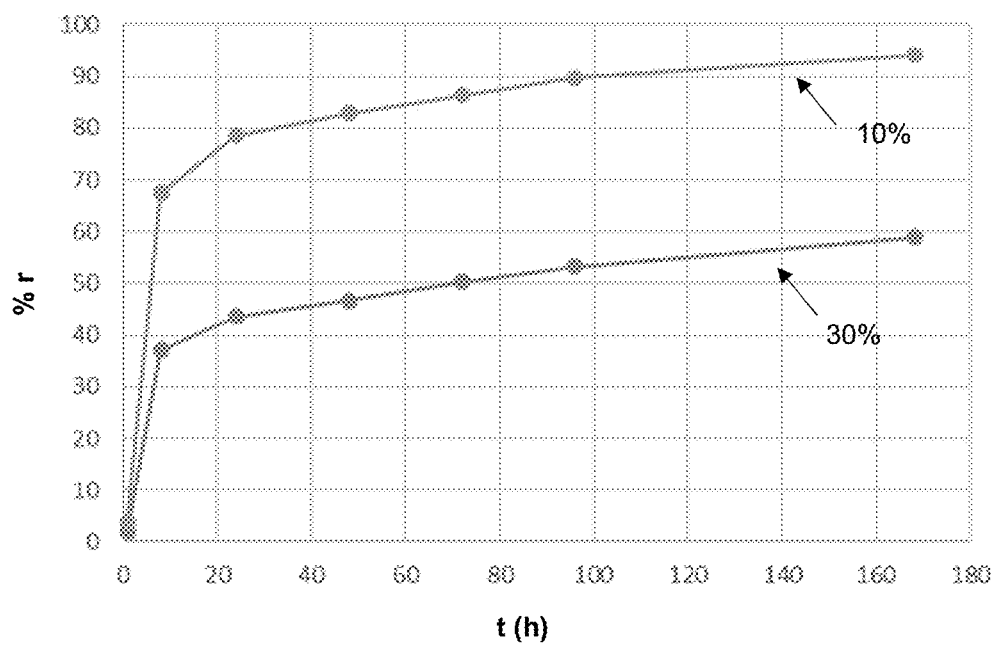
FIG. 10 shows the in vitro release of the active agent (% of the total load) overtime (hours) of a beaded membrane showing a shrinkage of about 10% (analog membrane to membrane 3 of table 1) and a non-beaded membrane showing a shrinkage of about 30% (analog membrane to membrane 2 of table 1).

Besides, the fact that the beaded membrane of the invention shows lower shrinkage, has also an impact on the release of the active agent. Thus, as can be seen in FIG. 10, a beaded membrane showing a shrinkage of about 10% allows a faster and complete sustained and controlled release of the active agent in comparison to a non-beaded membrane showing a shrinkage of about 30%.

In one embodiment, optionally in combination with one or more features of the various embodiments described above or below throughout all the description, the active agent contained in the nonwoven membrane of the invention, particularly SN-38, is present in the form of particles having an average particle size from 0.1 to 200 µm, more particularly from 1 to 100 µm, even more particularly from 1 to 25 µm. At least 90% by volume of the particles (Dv (90)) have a particle size equal to or below 23.6 µm.

The particle size can be determined by laser diffraction for instance using a Malvern Mastersizer Apparatus 3000 equipped with a HydroSM dispersion unit. Ethanol may be used as dispersion medium.

The beaded nonwoven membrane of the invention may be loaded with high amount of active agent. In one embodiment, optionally in combination with one or more features of the various embodiments described above or below throughout all the description, the active agent, particularly SN-38, is comprised in the membrane in an amount from 0.01 to 20%, more particularly from 0.1 to 5%, more particularly from 0.5 to 2%, by weight with respect to the total weight of the nonwoven membrane.

The load of the active agent in the membrane can also be expressed as weight of active agent per surface area of the beaded membrane. For example, for a membrane of 4 mg/cm$^2$ a load of 0.625% by weight with respect to the total weight of the nonwoven membrane would correspond to a load of 25 µg/cm$^2$.

As mentioned above, the inventors have surprisingly found that the presence of beads in the nonwoven membrane significantly reduces shrinkage of an analogous bead-free nonwoven membrane. Thus, in one particular embodiment, optionally in combination with one or more features of the various embodiments described above or below, the linear shrinkage in water at 37° C. of the beaded nonwoven membrane of the invention is reduced at least 50% with respect to an analog bead-free membrane.

In one embodiment, optionally in combination with one or more features of the various embodiments described above or below throughout all the description, the beaded nonwoven membrane of the invention has a degree of linear shrinkage in water at 37° C. and 72 h equal to or lower than 20% when the membrane is contacted with an appropriate amount of water-based medium in which the active agent is solubilized. As mentioned above, the degree of linear shrinkage is expressed as a percentage with respect to the original dimension and can be calculated by dividing the linear dimensions of the membrane (height and width) before shrinking and after shrinking with a physical measurement tool.

The beaded nonwoven membrane of the invention is capable of releasing the active agent thereof in a controlled and sustained manner when is contacted with an appropriate amount of medium in which the active agent is solubilized. When the beaded membrane of the invention is placed in the area of the body to be treated, the physiological medium acts as the appropriate medium that solubilizes the active agent in a sustained and controlled manner.

The term "controlled and sustained" release designates a gradual release at a predetermined time and at a desired rate during a predetermined release period. Typically, it means that the release of the drug takes place at such rate that the blood (e.g. plasma) concentration is maintained below toxic concentrations over a period of time of about 12 hours or longer.

In one embodiment, optionally in combination with one or more features of the various embodiments described above or below throughout all the description, the beaded nonwoven membrane of the invention is capable of releasing an amount equal to or greater than 80% of the total weight of the active agent, particularly SN-38, in a period which is equal or less than 50% of the degradation time of the polymeric nanofibers after contacting it with an appropriate amount of medium in which the active agent is solubilized. This way it is ensured that the active agent is released independently of the degradation of the polymeric nanofibers. More particularly, the beaded nonwoven membrane of the invention is capable of releasing an amount equal to or greater than 80% of the total weight of the active agent within 2.5 months, more particularly within 2 months, and even more particularly within 1.5 months or 1 month, 4 weeks, 3 weeks, 2 weeks or 1 week.

In another embodiment, optionally in combination with one or more features of the various embodiments described above or below throughout all the description, the beaded nonwoven membrane of the invention is capable of releasing an amount equal to or greater than 80%, more particularly 90%, even more particularly 100%, of the total weight of the active agent, particularly SN-38, in a period which equal or lower than 5 weeks.

In another embodiment, optionally in combination with one or more features of the various embodiments described above or below throughout all the description, the polymeric nanofibers of the membrane are totally degraded after contacting the membrane with an appropriate amount of medium in which the active agent is solubilized in 2, 3, 4, 4.5, or 5 months.

In another embodiment, optionally in combination with one or more features of the various embodiments described above or below throughout all the description, the beaded nonwoven membrane of the invention is capable of releasing an amount equal to or greater than 80%, more particularly 90%, even more particularly 100%, of the total weight of the active agent, particularly SN-38, in a period which equal or lower than 5 weeks; and the polymeric nanofibers of the membrane are totally degraded after contacting the membrane with an appropriate amount of medium in which the active agent is solubilized in 2, 3, 4, 4.5, or 5 months.

In another embodiment, optionally in combination with one or more features of the various embodiments described above or below throughout all the description, the beaded nonwoven membrane of the invention is capable of releasing an amount equal to or greater than 80%, more particularly 90%, even more particularly 100%, of the total weight of the active agent, particularly SN-38, in a period which equal or lower than 1.5 weeks, more particularly equal or lower than 7 days.

In another embodiment, optionally in combination with one or more features of the various embodiments described above or below throughout all the description, the beaded nonwoven membrane of the invention is capable of releasing an amount equal to or greater than 70% of the total weight of the active agent, particularly SN-38, in a period which equal or lower than 6 days, more particularly 5 days.

In another embodiment, optionally in combination with one or more features of the various embodiments described above or below throughout all the description, the beaded nonwoven membrane of the invention is capable of releasing an amount equal to or greater than 60% of the total weight of the active agent, particularly SN-38, in a period which equal or lower than 5 days, more particularly 4 days.

In another embodiment, optionally in combination with one or more features of the various embodiments described above or below throughout all the description, the beaded nonwoven membrane of the invention is capable of releasing an amount equal to or greater than 50% of the total weight of the active agent, particularly SN-38, in a period which equal or lower than 4 days, more particularly 3 days.

In another embodiment, optionally in combination with one or more features of the various embodiments described above or below throughout all the description, the beaded nonwoven membrane of the invention is capable of releasing an amount equal to or greater than 20% of the total weight of the active agent, particularly SN-38, in a period which equal or lower than 2 days, more particularly 1 day.

In another embodiment, optionally in combination with one or more features of the various embodiments described above or below throughout all the description, the beaded nonwoven membrane of the invention is capable of releasing an amount equal to or greater than 20% of the total weight of the active agent, particularly SN-38, in a period which equal or lower than 2 days; an amount equal to or greater than 50% in a period which equal or lower than 4 days; an amount equal to or greater than 60% in a period which equal or lower than 5 days; an amount equal to or greater than 70% in a period which equal or lower than 6 days; and an amount equal to or greater than 80% in a period which equal or lower than 1.5 weeks.

Generally, the release of the active agent at a specific time can be measured either a) by immersing a given nonwoven membrane into a medium in which the active agent is solubilized and measuring the concentration of active agent at the desired time (e.g. by high performance liquid chromatography, HPLC). Alternatively, b) by immersing a given nonwoven membrane into a medium in which the active agent is solubilized, waiting for the desired time, extracting the membrane from the medium and measuring the residual content of active agent by immersing the membrane in a known volume of a solvent (e.g. HFIP) which is able to dissolve the nanofibers of the membrane and measuring the concentration of active agent that remains in this solution (e.g. by HPLC).

In another embodiment, optionally in combination with one or more features of the various embodiments described above or below, the polymeric nanofibers of the beaded membrane are cylindrical and have an mean diameter from 50 to 2000 nm, more particularly from 200 to 1400 nm, from 500 to 1100 nm, and even more particularly they have an mean diameter of about 800 nm. For the purposes of the present invention, the term "mean diameter" relates to the diameter obtained by the arithmetic average of different measurements, e.g. 50 measurements, on an image obtained by Scanning Electron Microscope (SEM).

In another embodiment, optionally in combination with one or more features of the various embodiments described above or below throughout all the description, the beaded membrane of the invention has a thickness from 0.02 to 3 mm, more particularly from 0.02 to 2, from 0.02 to 1, from 0.02 to 0.5, from 0.05 to 0.5, or from 0.05 to 0.2 mm.

The beaded nonwoven membranes of the invention may be prepared by electrospinning or other technologies able to produce nanofibers. In one embodiment, optionally in combination with one or more features of the various embodiments described above or below throughout all the description, the polymeric nanofibers of the membrane are electrospun nanofibers, i.e. nanofibers obtained by an electrospinning process.

The polymeric nanofibers of the beaded nonwoven membrane of the invention consist of one or more polymers, more particularly 1, 2, 3 or 4 polymers.

Thus, in one embodiment, optionally in combination with one or more features of the various embodiments described above or below throughout all the description, the beaded nonwoven membrane comprises polymeric nanofibers made of a single polymer.

Alternatively, in another embodiment, optionally in combination with one or more features of the various embodiments described above or below throughout all the description, the beaded nonwoven membrane comprises polymeric nanofibers made of a combination of more than one polymer.

In another embodiment, optionally in combination with one or more features of the various embodiments described above or below throughout all the description, the polymers of the polymeric nanofibers are biocompatible. For the purposes of the invention the term "biocompatible polymer" refers to a polymer which in the amounts in which it is used does not cause adverse effects or harm to living tissues. Thus, a biocompatible polymer is non-toxic, chemically inert, and it does not cause any immune response or any other biological response such as the formation of scar tissue, or other inflammatory responses.

In another embodiment, optionally in combination with one or more features of the various embodiments described above or below throughout all the description, the polymers of the polymeric nanofibers are biodegradable. The term "biodegradable polymer" as used in the context of the present invention refers to a polymer that is degraded under physiological conditions, e.g. a biodegradable polymer may be broken down by cellular machinery. More particularly, the biodegradable polymers are stable for at least 30 days, more particularly for at least 15 days, when implanted and are fully degraded within 5, more particularly within 4, more particularly within 3 months, when implanted.

Non limiting examples of suitable polymers that may be used for forming the nanofibers include polyesters, polyanhydrides, polyphosphazenes, polyethers, and the like. In one embodiment, optionally in combination with one or more features of the various embodiments described above or below throughout all the description, the polymeric nanofibers are made of one or more polymers selected from the group consisting of polyglycolic acid (PGA), poly-D,L-lactic acid (PLA), poly-L-lactic acid (PLLA), poly-D,L-lactide-co-glycolide (PLGA), polycaprolactone (PCL), polyethylene glycol (PEG), polydioxanone (PDO), polyvinylalcohol (PVA), collagen, cellulose, hyaluronic acid, polyamide, polyester, polyurethane, polypropylene, elastane, silk, and a combination thereof. More particularly, the polymeric nanofibers are made of one or more polymers selected from the group consisting of polyglycolic acid (PGA), poly-D,L-lactic acid (PLA), poly-L-lactic acid (PLLA), poly-D,L-lactide-co-glycolide (PLGA), polycaprolactone (PCL), polyethylene glycol (PEG), silk, and a combination thereof.

Typically, the molecular weight (MW) of PLA is from 17 to 100 kg/mol, and the MW of PLGA is from 50 to 200 kg/mol. These polymers have a degradation time below one year.

In another embodiment, optionally in combination with one or more features of the various embodiments described above or below throughout all the description, the polymeric nanofibers are made of a combination of polymers selected from the group consisting of PLGA combined with PLA, PLGA combined with PEG, and PLGA combined with PCL. More particularly, the polymeric nanofibers are made of a combination of polymers selected from the group consisting of PLGA and PLA in an amount from 10:90 to 90:10 w/w; PLGA and PEG in an amount from 60:40 to 98:2 w/w; and PLGA and PCL in an amount from 10:90 to 90:10 w/w, wherein the ratios are given in weight of the polymer with respect to the total weight of the two polymers forming the combination.

As used herein, the term PLGA XX/YY refers to a PLGA wherein XX represents the lactide content, and YY represents the glycolide content, the ratio lactide/glycolide being expressed in mol percent. In one embodiment, optionally in combination with one or more features of the various embodiments described above or below throughout all the description, the lactide content XX is from 5% to 95%, and the glycolide content YY is form 95% to 5%, being the sum of XX and YY 100%.

In one embodiment, optionally in combination with one or more features of the various embodiments described above or below throughout all the description, the polymeric nanofibers are made of poly-D,L-lactide-co-glycolide (PLGA), more particularly, PLGA 75/25, and even more particularly a PLGA having a molecular weight (MW) from 50 to 200 kg/mol.

In another embodiment, optionally in combination with one or more features of the various embodiments described above or below throughout all the description, the polymeric nanofibers are made of poly-D,L-lactic acid (PLA), more particularly PLA having a molecular weight (MW) from 17 to 100 kg/mol.

As mentioned above, the active agent comprised in the beaded nonwoven membrane of the invention has water solubility equal to or lower than 33 mg/mL. Therefore, according to the standards of the art, the active agents considered in the present invention include active agents which are practically insoluble in water (water solubility of less than 0.1 mg/mL), very slightly soluble (water solubility from 0.1 to 1 mg/mL), slightly soluble (water solubility from 1 to 10 mg/mL), or sparingly soluble (water solubility from 10 to 33 mg/mL).

In one embodiment, optionally in combination with one or more features of the various embodiments described above or below throughout all the description, the active agent has a water solubility of 0.001-33 mg/mL.

Non-limiting examples of active agents include, without limitation, chemotherapeutic agents, such as SN-38 (7-ethyl-10-hydroxycamptothecin), paclitaxel, cisplatin, carboplatin, etoposide, carmustine, melphalan, camptothecin, 5-fluorouracile, methotrexate, erlotinib, gefitinib, sunitinib, vandetanib, dasatinib, lapatinib, imatinib (4-[(4-methylpiperazin-1-yl)methyl]-N-[4-methyl-3-[(4-pyridin-3-ylpyrimidin-2-yl)amino]phenyl]benzamide), imatinib mesylate (4-[(4-methylpiperazin-1-yl)methyl]-N-[4-methyl-3-[(4-pyridin-3-ylpyrimidin-2-yl)amino]phenyl]benzamide methanesulfonic acid), nutlin, gemcitabine, docetaxel, bortezomib, valproic acid, vismodegib, cinacalcet, trabectedin, topotecan, MLN4924, olaparib, iniparib, arsenic trioxide, crizotinib, celecoxib, perifosine, rapamycin, temsirolimus and everolimus; nutraceuticals, such as curcumin, resveratrol, genistein and quercetin; antibiotics or antifungals, such as chloramphenicol, Penicillin G Procaine, fusidic acid, mebendazol and albendazol; proteins including growth factors, such as insulin, PDGF, TGF-B, EGF, VEGF, IGF-I, bFGF and HGF; cells (autogenic or allogenic cells being differentiated cells or stem cells), immunotherapy agents, anti-infectious agents, endocrine agents and cardiovascular agents.

In one embodiment, optionally in combination with one or more features of the various embodiments described above or below throughout all the description, the nonwoven membrane of the invention comprises more than one active agent, more particularly the membrane comprises a second active agent.

Depending on the active agents used, the beaded nonwoven membrane of the invention may be used for therapeutic purposes. In the context of the present invention, the term "therapeutic" means that it is therapeutically useful, for example, in the treatment, remission or attenuation of a disease state, physiological state, or their symptoms or for the evaluation or diagnosis thereof.

In one embodiment, optionally in combination with one or more features of the various embodiments described above or below throughout all the description, the active agent comprised in the beaded nonwoven membrane is a therapeutic agent, which can be used both in the pharmaceutical field and in the veterinary field. More particularly, the active agent is a chemotherapeutic agent.

For the purposes of the invention, the term "chemotherapeutic agent" refers to an agent or drug that inhibits tumor cell growth and/or induces tumor cell death.

In one embodiment, optionally in combination with one or more features of the various embodiments described above or below throughout all the description, the active agent comprised in the beaded nonwoven membrane is a therapeutic agent selected from the group consisting of: SN-38 (7-ethyl-10-hydroxycamptothecin), paclitaxel, cisplatin, carboplatin, etoposide, carmustine, melphalan, camptothecin, 5-fluorouracile, methotrexate, erlotinib, gefitinib, sunitinib, vandetanib, dasatinib, lapatinib, imatinib (4-[(4-methylpiperazin-1-yl)methyl]-N-[4-methyl-3-[(4-pyridin-3-ylpyrimidin-2-yl)amino]phenyl]-benzamide), imatinib mesylate (4-[(4-methylpiperazin-1-yl)methyl]-N-[4-methyl-3-[(4-pyridin-3-ylpyrimidin-2-yl)amino]phenyl]benzamide methanesulfonic acid), nutlin, gemcitabine, docetaxel, bortezomib, valproic acid, vismodegib, cinacalcet, trabectedin, topotecan, MLN4924, olaparib, iniparib, arsenic trioxide, crizotinib, celecoxib, perifosine, rapamycin, temsirolimus, and everolimus. More particularly, the active agent is SN-38.

The beaded membrane of the invention may be formed by only one layer of polymeric nanofibers, or alternatively, it may be formed by a plurality of layers, wherein at least one of the layers comprising one active agent.

In one embodiment, optionally in combination with one or more features of the various embodiments described above or below throughout all the description, the beaded nonwoven membrane of the invention comprises or consists of one first layer comprising polymeric nanofibers in the absence of active agents, a second layer comprising polymeric nanofibers and at least one active agent, and a third layer comprising polymeric nanofibers in the absence of active agents.

When the beaded nonwoven membrane comprises different layers of polymeric nanofibers, the nanofibers of each of the layers can be made of equal or different polymers, they may have equal or different nanofiber diameters, and each of the layers may have equal or different thickness. Besides, if more than one layer is loaded with one or more active agents, the active agents may be the same or different. Additionally, when the beaded nonwoven membrane comprise different layers of polymeric nanofibers, it is also possible to have a drug layer free of polymeric nanofibers which is placed between two layers of polymeric nanofibers.

In one embodiment, optionally in combination with one or more features of the various embodiments described above or below throughout all the description, the beaded nonwoven membrane comprises or consists of a first layer comprising polymeric nanofibers, a second layer comprising polymeric nanofibers and at least one active agent, and a third layer comprising polymeric nanofibers. More particularly, the beaded nonwoven membrane consists of a first layer consisting of polymeric nanofibers, a second layer consisting of polymeric nanofibers and at least one active agent, and a third layer consisting of polymeric nanofibers. Even more particularly, the nanofibers of each of the three layers are made of the same polymers, and have the same nanofiber diameters.

Optionally, the beaded nonwoven membrane of the invention as previously defined can be coated on one side in order to achieve a unidirectional release towards one face of the membrane. Thus, in one embodiment, optionally in combination with one or more features of the various embodiments described above or below throughout all the description, the beaded nonwoven membrane of the invention is coated on one side. Typically, the coating may be carried out by one of the following methods: adhesion with biocompatible glue, contact with polymer solvent such as methylene chloride, chloroform, ethyl acetate, acetone, dimethylformamide, dimethylsulfoxide, for example; mechanical punch, or electrospinning parameters that favours fibre adhesion.

As mentioned above, thanks to the reduced shrinkage, the beaded nonwoven membrane of the invention has an improved drapability e.g. to the organ or surgical site when the delivery agent is a therapeutic agent. For the purposes of the invention, the term "drapability" refers to the capacity of the material to mold to irregular, curved surfaces or surfaces of other geometries. This property may help in avoiding any possible lesions produced by an excessive rigidity of the membrane in the area where it is implanted.

The beaded nonwoven membrane of the invention can be prepared by a process, which comprises the following steps:
  a) preparing a solution of one or more polymers in a suitable solvent system;
  b) preparing a solution or a suspension of the active agent in a suitable solvent system, particularly wherein the polymer or polymers from step a) are insoluble;
  c) carrying out the electrospinning of the solution from step a) to produce beaded polymeric nanofibers, and, simultaneously, depositing the solution or suspension of step b) over the polymeric nanofibers; and
  d) optionally, drying the nonwoven membrane obtained from step c).

The beaded morphology of the nonwoven membrane of the invention results from the conditions used in the electrospinning process. Generally speaking, beads are formed in the electrospinning process when the polymer solution has a low viscosity, but not low enough to produce electrospray (i.e. drops instead of fibers). The viscosity of the polymer solution may be tuned with the concentration of the polymer in the solution: higher concentrations provide higher viscosity and lower concentrations provide lower viscosity.

Without being bound to theory, it is thought that when the viscosity is low the high surface tension overcomes the viscosity, which leads to the formation of beads. The number and distribution of beads may also be tuned by adjusting other process parameters such as for example the applied voltage or the spinning needle diameter. Thus, the skilled person will know how to adjust the parameters to obtain the desired number of beads. For example, for a given polymer and a given solvent easy experiments can be carried out varying the concentration of the polymer and analyzing the number of beads by SEM (or shrinkage degree) in the final membrane, and determine the optimal conditions to be used for each polymer and solvent.

In one embodiment, optionally in combination with one or more features of the various embodiments described above or below throughout all the description, in step a) the concentration of polymer is such that beads along the nanofiber are formed in step c).

In another embodiment, optionally in combination with one or more features of the various embodiments described above or below throughout all the description, in step a) the concentration of polymer is from 0.5 to 2% lower than the concentration that it would be used for preparing an analog bead-free polymeric nonwoven membrane comprising the same active agents and polymers and under the same process conditions, particularly lower than the lower concentration that it would be used for preparing an analog bead-free polymeric nonwoven membrane comprising the same active agents and polymers and under the same process conditions. For example, if for a given bead-free polymeric nonwoven membrane, a concentration of polymer of 9% w/w (i.e. 9 g polymer/100 g solvent) is used, then for the preparation of the analog beaded membrane, the concentration of polymer could be of 7%.

Some examples of suitable solvent systems for dissolving the polymer (step a of the process) include, without limitation, dichloromethane, chloroform, ethyl acetate, acetone, dimethylformamide, dioxane, dimethylsulfoxide (DMSO), 1,1,1,3,3,3-hexafluoroiso-propanol (HFIP) or mixtures thereof. The solvent system for dissolving the polymer may optionally include additives to improve the electrospinning process, such as surfactant agents or salts (e.g. NaCl). Particularly, the salts are present in a concentration which is equal to or lower than 0.2 g/mL).

Non-limiting examples of surfactants that may be added to the polymer solution include, non-ionic surfactants such as block polymer nonionic surfactant (poloxamers, meroxapols, and poloxamines)phosphatidylcholine, phosphatidylethanolamine, lecithin, polyvinyl alcohol, polyvinylpyrrolidone, polysorbate 80 and the like. The surfactant may be added at a concentration from 0.01 to 10%, more particularly, 2% by weight of total weight of solution.

A scheme of the chemical structure of poloxamers, meroxapols, and poloxamines is shown below:

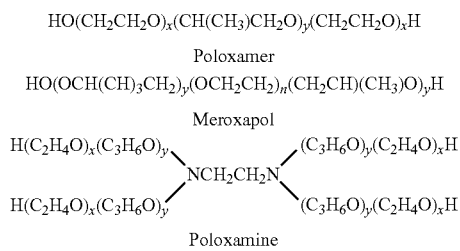

Poloxamers, also known as pluronic compounds, are nonionic triblock copolymers composed of a central hydrophobic chain of polyoxypropylene (poly(propylene oxide)) (PPO) flanked by two hydrophilic chains of polyoxyethylene (poly(ethylene oxide)) (PEO). Non-limiting examples of poloxamers include Pluronic® F68 (also known as Kolliphor® P 188, Lutrol® F68, Synperonic® F68 or Poloxamer 188), Pluronic® F127, Pluronic® F108, Pluronic® L101, Pluronic® L121, Pluronic® P85, Pluronic® Pl 05 or Pluronic® P123), and the like.

Meroxapols have a different structure from poloxamers. Thus, while the poloxamer structure is terminated by two primary hydroxyl groups, the meroxapol series has secondary hydroxyl groups at the ends. In the poloxamer series the hydrophobe is on the inside, while the corresponding meroxapol has the hydrophobe split in two.

Poloxamines (Tetronic) are X-shaped amphiphilic block copolymers formed by four arms of poly(ethylene oxide)-poly(propylene oxide) (PEO-PPO) blocks bonded to a central ethylenediamine moiety. Non-limiting examples of poloxamines include Tetronic® T1307, Tetronic® T1107 or Tetronic® T904.

Thus, in one particular embodiment, optionally in combination with one or more features of the various embodiments described above or below, the beaded nonwoven membrane of the invention further comprises a surfactant. More particularly, a surfactant selected from the groups consisting of poloxamer, meroxapol, poloxamine, phosphatidylcholine, phosphatidylethanolamine, lecithin, polyvinyl alcohol, polyvinylpyrrolidone, polysorbate 80, and combinations thereof.

The polymer concentration is generally adjusted for a given solvent system to obtain beads. For example, when the polymeric nanofibers are prepared from a solution of PLGA75/25 in HFIP the appropriate concentration may range from 6 to 8% w/w. When the polymeric nanofibers are prepared from a solution of PLGA75/25 in dioxane/acetone (40%/60% w/w) the appropriate concentration may range from 15 to 20% w/w. When the polymeric nanofibers are prepared from a solution of PLA in dichloromethane, the appropriate concentration may range from 8 to 12% w/w.

In step b) the active agent is dissolved or suspended, particularly suspended, in a solvent system that is not capable of solubilizing the polymer or polymers employed in step a). Thus, the solvent system of step b) is different from the solvent system of step a). Also, the solvent of step b) must be compatible with the desired active agent so as not to cause its degradation (e.g. acetate buffer).

Optionally, surfactants or salts such as the ones mentioned above can be added to the solution or suspension of the active agent.

Alternatively, the surfactant may also be added to the polymer solution of step a) to improve the electrospinning process, or to both the polymer solution of step a) and the active agent solution of step b).

Thus, in one particular embodiment, optionally in combination with one or more features of the various embodiments described above or below, the process for the preparation of the beaded nonwoven membranes of the invention comprises the following steps:
a) preparing a solution of one or more polymers in a suitable solvent system optionally containing a surfactant;
b) preparing a solution or a suspension of the active agent in a suitable solvent system optionally containing a surfactant, particularly wherein the polymer or polymers from step a) are insoluble;
c) carrying out the electrospinning of the solution from step a) to produce beaded polymeric nanofibers, and, simultaneously, depositing the solution or suspension of step b) over the polymeric nanofibers; and
d) optionally, drying the nonwoven membrane obtained from step c).

In one more particular embodiment, the solution of step a) further comprises a surfactant. In another more particular embodiment, the solution or suspension of step b) further comprises a surfactant. In another more particular embodiment, both the solution of step a) and the solution or suspension of step b) further comprise a surfactant, wherein the surfactant used in step a) and the surfactant used in step b) may be the same or different.

In step c) of the process of the invention the electrospinning of the solution from step a) is carried out to produce beaded polymeric nanofibers. The polymeric nanofibers are deposited on a collector (which may be a rotating cylinder or any other collector that oscillates between the deposition zones of the electrospinning. The expert in the art will be able to routinely adjust the suitable solvents both to prepare the polymeric solution such as the active agent solution, as well as the suitable parameters of the electrospinning process to obtain a beaded nonwoven membrane with appropriate characteristics for the desired application.

In one embodiment, optionally in combination with one or more features of the various embodiments described above or below throughout all the description, the voltage tension difference applied between the jet and the collector during electrospinning is from 8 to 20 kV, more particularly, from 10 to 14 KV.

In another embodiment, optionally in combination with one or more features of the various embodiments described above or below throughout all the description, the electrospinning is carried out for a time period from 30-500 min, more particularly from 200 to 400 min.

In another embodiment, optionally in combination with one or more features of the various embodiments described above or below throughout all the description, the flow rate of the polymer solution is from 1-6 mL/h, more particularly from 2 to 4 mL/h.

In another embodiment, optionally in combination with one or more features of the various embodiments described above or below throughout all the description, the tip of the needle was placed at a distance from 90 to 120 mm from the metallic rotating cylinder.

In another embodiment, optionally in combination with one or more features of the various embodiments described above or below throughout all the description, the voltage tension difference applied between the jet and the collector during electrospinning is from 8 to 20 kV, more particularly, from 10 to 14 KV; the flow rate of the polymer solution is from 1-6 mL/h, more particularly from 2 to 4 mL/h; the tip of the needle was placed at a distance from 90 to 120 mm from the metallic rotating cylinder; and the polymeric nanofibers are prepared either from a solution of PLGA75/25 in HFIP at a concentration from 6 to 8% w/w, or alternatively from a solution of PLGA75/25 in dioxane/acetone (40%/60% w/w) at a concentration from 15 to 20% w/w, or alternatively from a solution of PLA in dichloromethane, at a concentration from 8 to 12% w/w. More particularly, in this embodiment, the active agent is SN-38, more particularly having a particle size from 1 to 25 µm.

During the electrospinning of the polymer solution is carried out, the solution or suspension of step b) is deposited over the resulting polymeric nanofibers such that the active agent is retained in the beaded nonwoven membrane.

The deposition of the active agent solution or suspension may be performed by different methods such as by spraying the solution (either by spray or electrospray); by pouring it by gravity (the active agent particles can be dosed for example by vibration of a sieve or by leaving drops of suspension or solution); or by means of a µL dispenser (any mechanical method dosing may be used).

When a solution or suspension of active agent is used, said drops are deposited on the nanofibers that coat the collector. Once the solvent of the drops evaporates, the active agent is in solid form, forming either a coating to the fibres or solid particles that can have crystalline or amorphous structure.

When a spray system is used, the spray system for depositing the active agent operates in the flow rates and viscosities determined by the active agent itself, and may be for example, an electrospray system, pneumatic spray, ultrasonic spray or combined spray pneumatic/ultrasound. In a particular embodiment, optionally in combination with one or more features of the various embodiments described in this invention, the spray system used is electrospray.

Figure 1C:
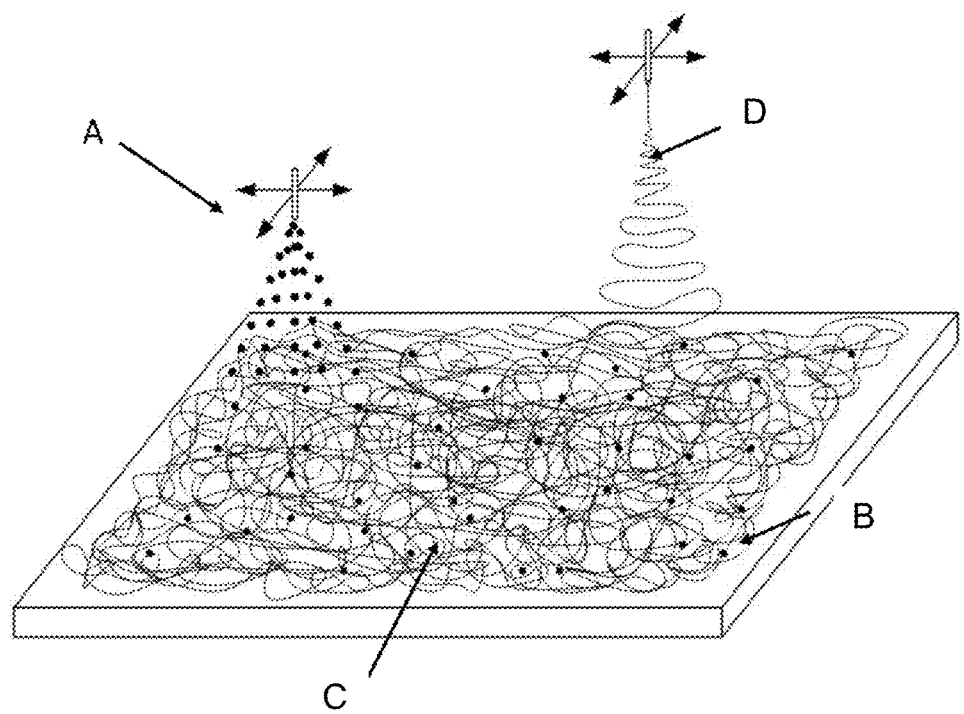
Figure 1D:
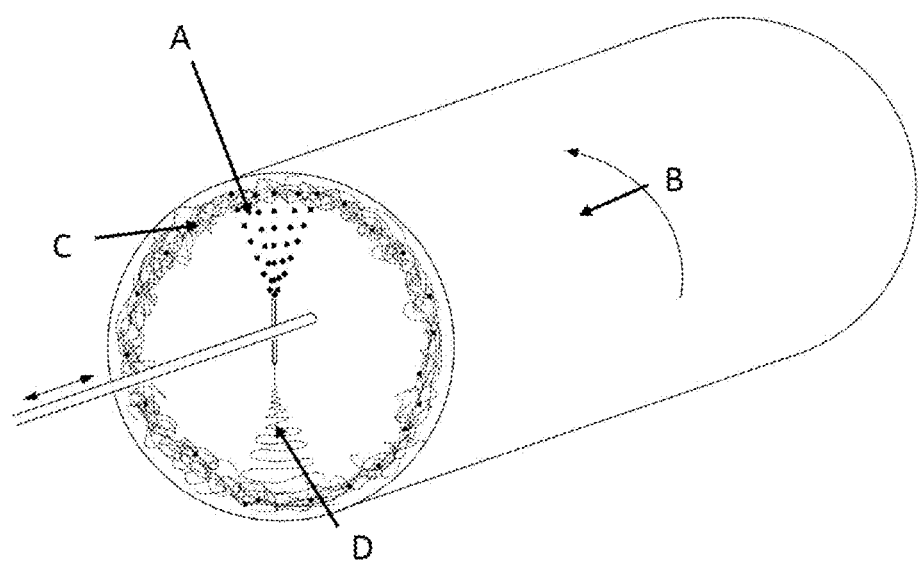

Furthermore, different configurations of the system may be used. FIG. 1 shows different ways to simultaneously incorporate the active agent in the membrane while nanofibers are produced. Thus, the deposition of the active agent may be carried out on a rotating cylindrical collector either along the horizontal axis (see FIG. 1A), or the vertical axis (see FIG. 1B). It may also be deposited on a static collector by moving fibre and active agent pouring devices (FIG. 1C). Alternatively, the active agent may also be deposited in the inner surface of a rotating collector (FIG. 1D).

Furthermore, the process can be carried out in different steps wherein successive layers of membrane with different concentrations of active agent are generated.

In a particular embodiment, optionally in combination with one or more features of the various embodiments described above and below throughout all the description, when the beaded nonwoven membrane consists of a first layer consisting of polymeric nanofibers, a second layer consisting of polymeric nanofibers and at least one active agent, and a third layer consisting of polymeric nanofibers, the process comprises the following steps:

A) preparing a first solution of one or more polymers in a suitable solvent system optionally containing a surfactant;

B) carrying out the electrospinning of the solution from step a) to produce a first layer of beaded polymeric nanofibers;

C) preparing a second solution of one or more polymers optionally containing a surfactant in a suitable solvent system;

D) preparing a solution or a suspension of the active agent in a suitable solvent system optionally containing a surfactant, particularly wherein the polymer or polymers from step a) are insoluble;

E) carrying out the electrospinning of the solution from step C) to produce beaded polymeric nanofibers, and, simultaneously, depositing the solution or suspension of step D) over the polymeric nanofibers, such that a second layer of polymeric nanofibers and active agent is deposited over the first layer;

F) preparing a third solution of one or more polymers in a suitable solvent system optionally containing a surfactant;

G) carrying out the electrospinning of the solution from step F) to produce a third layer of beaded polymeric nanofibers which is deposited over the second layer; and E) optionally, drying the beaded nonwoven membrane obtained from step G).

Generally, the process of electrospinning/electrospray is performed during a necessary time, with a flow polymeric solution and a flow rate of active agent solution such as to obtain the beaded nonwoven membrane containing active agent comprised in an amount from 0.01 to 20% by weight with respect to the total weight of the beaded nonwoven membrane.

After the solvents have been evaporated from the membrane, said membrane can be directly used. In a particular embodiment, the process of the invention comprises drying the nonwoven membrane obtained after the electrospinning/electrospray process, more particularly the drying step is performed by leaving to dry the solvents employed in the processes of electrospinning and electrospraying.

It also forms part of the invention a beaded nonwoven membrane comprising polymeric nanofibers, and at least one active agent, wherein the nanofibers comprise beads distributed along the nanofiber length and have a mean diameter which is from 1.5 to 20 times the mean diameter of the nanofiber, and wherein the active agent has a water solubility equal to or lower than 33 mg/mL; which is obtainable by a process which comprises the following steps:

a) preparing a solution of one or more polymers in a suitable solvent system;

b) preparing a solution or a suspension of the active agent in a suitable solvent system, particularly wherein the polymer or polymers from step a) are insoluble;

c) carrying out the electrospinning of the solution from step a) to produce beaded polymeric nanofibers, and, simultaneously, depositing the solution or suspension of step b) over the polymeric nanofibers; and d) optionally, drying the nonwoven membrane obtained from step c).

The beaded nonwoven membrane "obtainable by" the process as defined above is used herein to define the membrane by its preparation process and relates to the membrane obtainable by the preparation process which comprises the steps a), b), c) and d) described above. For the purposes of the invention, the expressions "obtainable", "obtained" and equivalent expressions are interchangeably used, and in any case the expression "obtainable" includes the expression "obtained".

The embodiments mentioned above with regard to the beaded nonwoven membrane and its preparation process also apply to the beaded nonwoven membrane obtainable by its preparation process.

As mentioned above, the beaded nonwoven membrane of the present invention may be used as a drug delivery system (DDS) for the treatment of diseases. Thus, it also forms part of the invention a beaded nonwoven membrane as previously defined for use as a medicament.

When the active agent contained in the beaded nonwoven membrane of the invention is a chemotherapeutic agent, it can be used in the treatment of tumors. Accordingly, the invention relates to beaded nonwoven membrane previously defined comprising an active agent for use in the treatment of tumors that include non-resectable areas with vital vessels; the treatment of surgical borders wherein tumor residues are left; the treatment of osseous tissues with tumor infiltration or positive bone scan; or in tissue regeneration; wherein the active agent is a chemotherapeutic agent.

This aspect of the invention can also be formulated as the use of an active agent for the preparation of a beaded nonwoven membrane as previously defined; for the treatment of tumors that include non-resectable areas with vital vessels; the treatment of surgical borders wherein tumor residues are left; the treatment of osseous tissues with tumor infiltration or positive bone scan; or in tissue regeneration; wherein the active agent is a chemotherapeutic agent.

The invention also relates to a method for the treatment of tumors that include non-resectable areas with vital vessels; the treatment of surgical borders wherein tumor residues are left; the treatment of osseous tissues with tumor infiltration or positive bone scan; or to a method for tissue regeneration, said method comprising the administration in said mammal, including a human, of the beaded nonwoven membrane as previously described, where the active agent in a chemotherapeutic agent.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1. Preparation of a Beaded PLGA Nonwoven Membrane Containing SN-38 (Electrospun from a PLGA Solution in HFIP)

1.1 Preparation of the Drug Suspension

SN-38 (4 mg) was suspended in acetate buffer, pH5, 15 mL under agitation.

1.2 Preparation of the Beaded Nonwoven Membrane

A beaded nonwoven membrane containing three layers of electrospun PLGA nanofibers (a first drug-free layer, a second drug-loaded layer, and a third drug-free layer deposited consecutively) was prepared.

Firstly, PLGA75/25 (95 kg/mol) was dissolved in 1,1,1,3,3,3-Hexafluoroiso-propanol (HFIP) at a concentration of 7% w/w. The solution was loaded in a syringe having a ⌀0.4 mm needle and introduced at a constant rate pump attached to the electrospinning machine. The tip of the needle was placed at a distance of 110 mm from the metallic rotating cylinder. Diameter of the collector was 120 mm.

To form the first (drug-free) PLGA layer, PLGA solution was electrospun for 7 min and collected over a vegetal paper substrate. The flow rate of PLGA solution was 4 mL/h and the voltage 12 kV.

Then, the second (drug-loaded) PLGA layer was formed onto the first layer by electrospinning additional 60 min of PLGA solution under the same conditions as the ones described for the first layer, while simultaneously electrospraying the drug suspension as prepared in 1.1. The drug solution was electrosprayed with a tension of 17 kV, a distance to the collector of 35 mm and a flow rate of 9 mL/hour.

Finally, the third (drug-free) PLGA layer was formed onto the second layer by electrospinning additional 7 min of PLGA solution under the same conditions as the ones described for the first layer.

Figure 2:
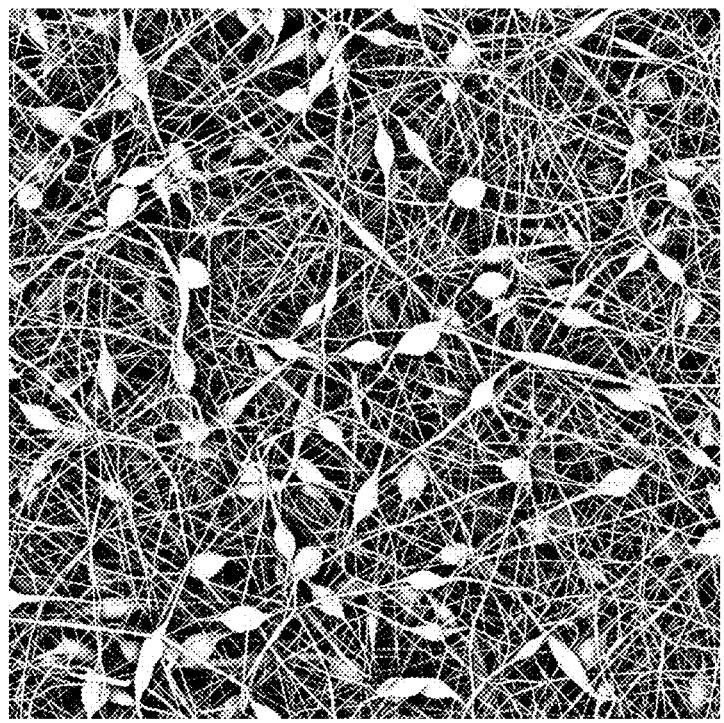
FIG. 2 shows a scanning electron micrograph of the beaded nonwoven membrane of example 1 at 1000× magnifications.

The obtained beaded nonwoven membrane was dried at room temperature and under vacuum for 24 h. FIG. 2 shows a scanning electron micrograph of the beaded nonwoven membrane obtained at 1000× magnifications. The PLGA nanofibers had a mean diameter of 852 nm, bead concentration was 1077 beads/mm$^2$, and bead diameter was 7 μm as determined by scanning electron microscopy; and the theoretical amount of SN-38 loaded was 0.1% by weight.

Example 2. Preparation of a Beaded PLGA Nonwoven Membrane Containing SN-38 (Electrospun from a PLGA Solution in Dioxane/Acetone)

The beaded nonwoven membrane was prepared following the same procedure as described in example 1 with the difference that the solvent used for dissolving the PLGA was a mixture of dioxane/acetone (40%/60% w/w) and that the polymer concentration was 16% w/w.

Figure 3:
FIG. 3 shows a scanning electron micrograph of the beaded nonwoven membrane of example 2 at 1000× magnifications.

FIG. 3 shows a scanning electron micrograph of the beaded nonwoven membrane obtained at 1000× magnifications. In the nonwoven membrane, the PLGA nanofibers had a mean diameter of 800 nm, as determined by scanning electron microscopy; and the theoretical amount of SN-38 loaded was 0.1% by weight.

Example 3. Preparation of a Beaded PLA Nonwoven Membrane Containing SN-38 (Electrospun from a PLA Solution in Dichloromethane)

The beaded nonwoven membrane was prepared following the same procedure as described in example 1 with the difference that PLA (high molecular weight) was used instead of PLGA; the solvent used for dissolving the PLA was dichloromethane; and the polymer concentration was 10% w/w.

Figure 4:
FIG. 4 shows a scanning electron micrograph of the beaded nonwoven membrane of example 3 at 1000× magnifications.

FIG. 4 shows a scanning electron micrograph of the beaded nonwoven membrane obtained at 1000× magnifications. In the nonwoven membrane, the PLGA nanofibers had a mean diameter of 700 nm, as determined by scanning electron microscopy; and the theoretical amount of SN-38 loaded was 0.1% by weight.

Comparative Example 4. Preparation of a Bead-Free PLGA Nonwoven Membrane Containing SN-38 (Electrospun from a PLGA Solution in HFIP)

A comparative bead-free nonwoven membrane was prepared according to the PCT application WO2013144206. Briefly, the bead-free nonwoven membrane was prepared following the same procedure as described in example 1 with the difference that concentration of PLGA in HFIP was 8.4% w/w instead of 7% used in example 1. The increase of concentration produced non-beaded membranes.

Figure 5:
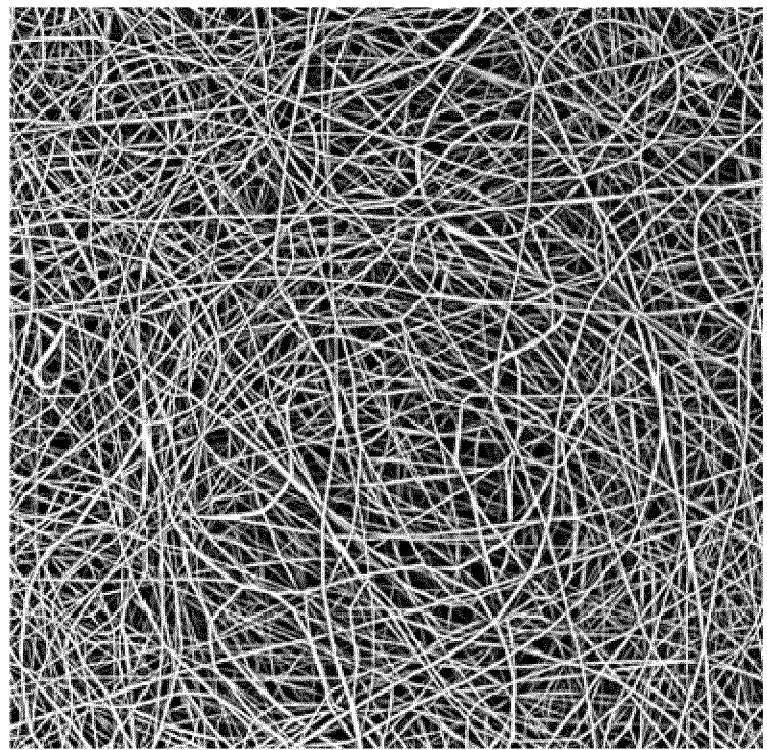
FIG. 5 shows a scanning electron micrograph of the bead-free nonwoven membrane of comparative example 4 at 1000× magnifications.

FIG. 5 shows a scanning electron micrograph of the bead-free nonwoven membrane obtained at 1000× magnifications. In the nonwoven membrane, the PLGA nanofibers had a mean diameter of 695 nm, as determined by scanning electron microscopy; and the theoretical amount of SN-38 loaded was 0.1% by weight

Example 5: Shrinkage Behaviour Comparative Study

The shrinkage behaviour of the beaded nonwoven membrane of example 1 according to the invention, and of the bead-free nonwoven membrane of comparative example 4 was compared.

For this purpose, 30×30 mm samples of each membrane were cut. Two pairs of points, separated 20 mm each, in longitudinal and cross section had been marked on the membranes (see FIG. 6, sample 21A). The samples were immersed in a bath of distilled water at constant temperature (37.0° C.) and the distance between the points of each sample was measured at fixed times at 24 h, 48 h and 72 h.

Figure 6:
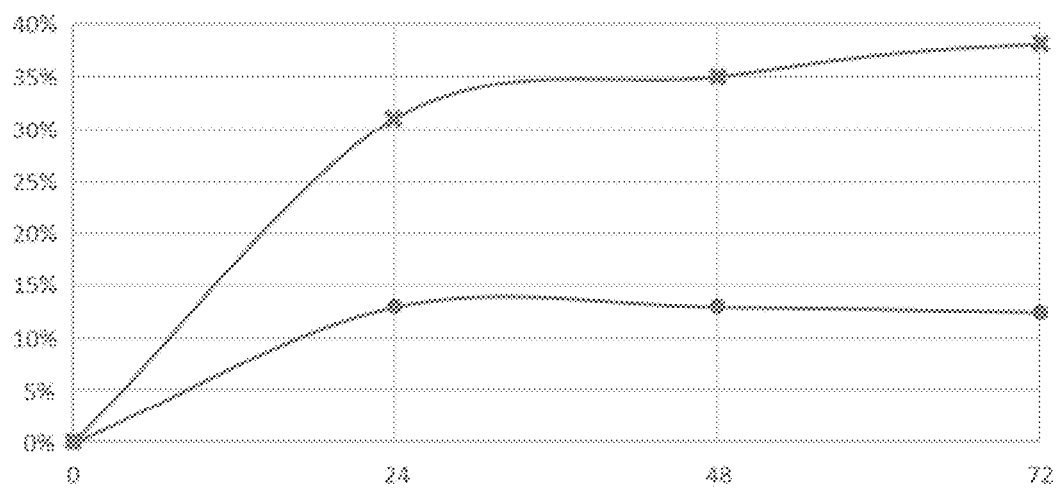
FIG. 6 shows the shrinkage behaviour (linear shrinkage over time in hours) of the beaded nonwoven membrane of example 1 according to the invention (circles), and of the bead-free nonwoven membrane of comparative example 4 (crosses).
Figure 7:
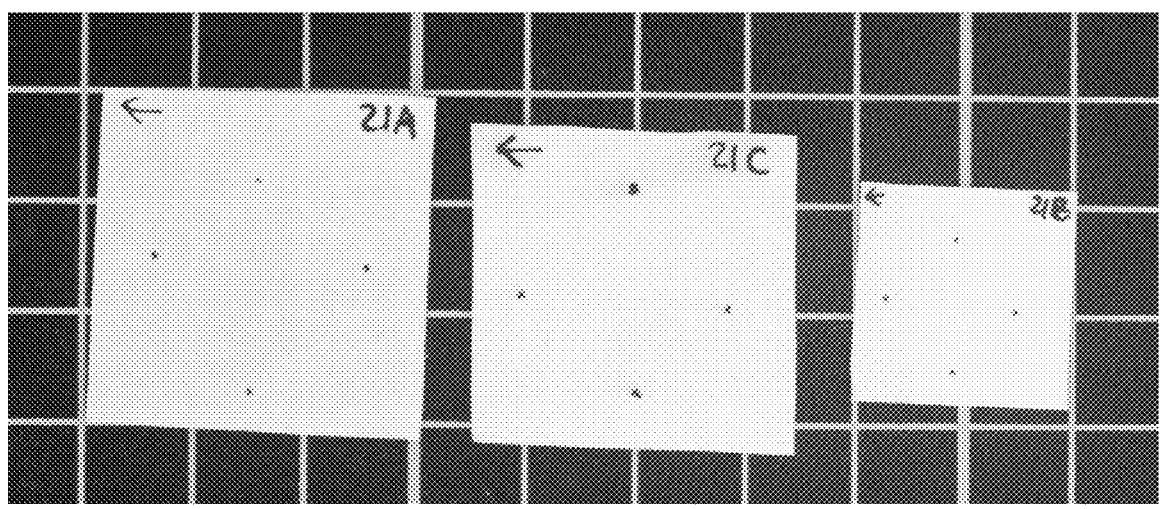
FIG. 7 shows the beaded nonwoven membrane of example 1 before incubation (21A) and after incubation during 48 h (21C), and the bead-free nonwoven membrane of comparative example 4 after incubation during 48 h (21B).
Figure 8A:
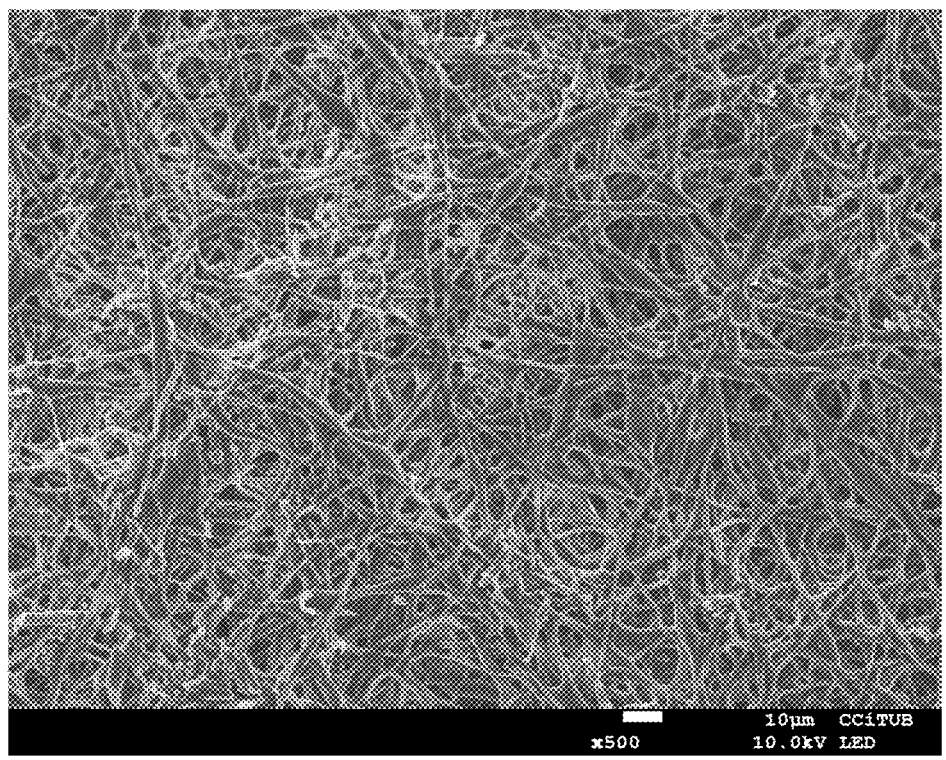
In FIG. 8A the beads can be clearly seen.
Figure 8B:
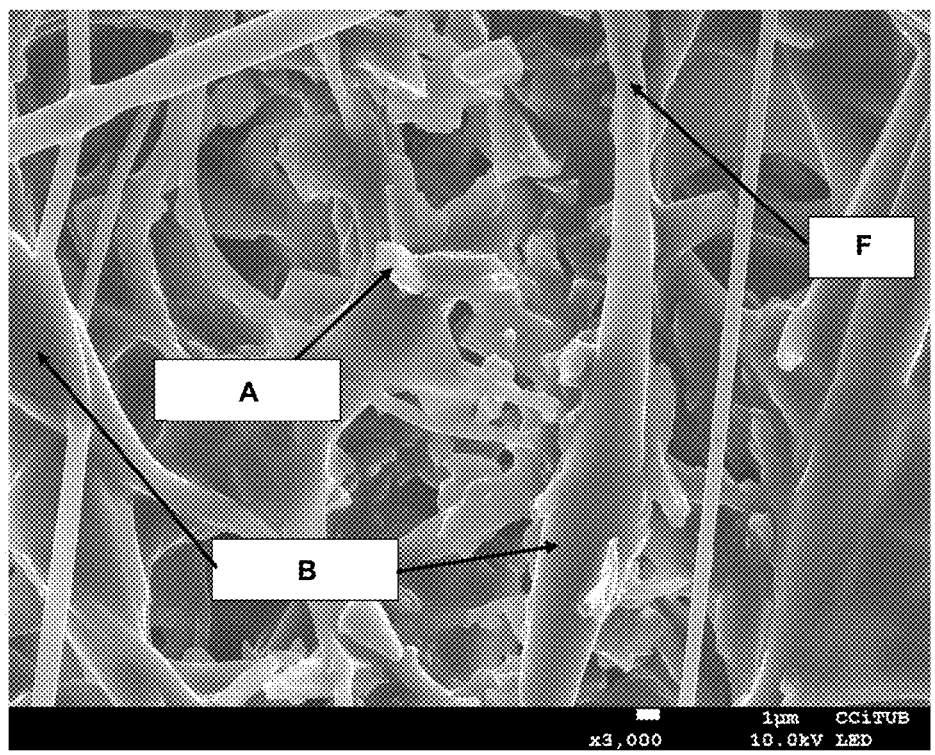
In FIG. 8B it is shown that the crystals of the active agent are externally arranged to the nanofibers, i.e. all the surface of the active agent is exposed to the medium.

FIG. 6 shows the linear shrinkage for the tested membranes over time. FIG. 7 shows the beaded nonwoven membrane of example 1 before incubation (21A) and after incubation during 48 h (21C), and the bead-free nonwoven membrane of comparative example 4 after incubation during 48 h (21B). The bead-free nonwoven membrane of comparative example 4 had the same size of the beaded nonwoven membrane of example 1 before incubation (21A). As can be seen from both figures, the beaded membrane did not significantly shrink while the bead-free membrane shrunk considerably.

Example 6: In Vitro Drug Release Comparative Study

The in vitro drug release of the active agent of nonwoven membranes 1-3 loaded with SN-38 having different degrees of shrinkage was compared. The release was assessed in Phosphate Buffered Saline (PBS) buffer pH 7.4 at 37° C., and 75 rpm stirring using the dissolution testing apparatus SOTAX, Model: AT 7 Smart. The volume of the media was 200 mL and it was replaced at days 1, 2, 3, 4 and 7 due to the low solubility of the drug.

Membrane 1 was prepared according to the process described in example 1 with the only difference that the PLGA concentration was 8%. Membrane 2 was prepared according to the process described in example 4 with the only difference that the PLGA concentration was 9%. Membrane 3 corresponds to the membrane of example 1. The obtained results are shown in the table 1 below:

TABLE 1

| Membrane Code | SN-38 load ($\mu g/cm^2$) | PLGA concentration in HFIP | % of linear shrinkage after 72 h of incubation | % of SN38 released at 96 h (with respect to the initial membrane content) | Average amount of beads visible in SEM per $mm^2$ | Average max diameter of beads [$\mu m$] |
|---|---|---|---|---|---|---|
| Membrane 1 | 25 | 8% | 18.8% | 66% | 500 | 3 |
| Membrane 2 | 25 | 9% | 28.6% | 57% | 0 | 0 |
| Membrane 3 (example 1) | 25 | 7% | 10.6% | 94% | 1500 | 5 |

As can be seen, the membranes showing lower shrinkage released the active agent at a much higher extent.

Example 7. In Vitro Release Assay

The in vitro release of the beaded membrane obtained in example 1 was assessed in Phosphate Buffered Saline (PBS) buffer pH 7.4 at 37° C., and 75 rpm stirring using the dissolution testing apparatus SOTAX, Model: AT 7 Smart. The volume of the media was 200 mL and it was replaced at days 1, 2, 3, 4 and 7 due to the low solubility of the drug. Besides, a comparative release assay in the conditions described above was also carried out for beaded membrane showing a shrinkage of about 10% (membrane analog to membrane 3 of table 1) and a non-beaded membrane showing a shrinkage of about 30% (membrane analog to membrane 2 of table 1).

Figure 9:
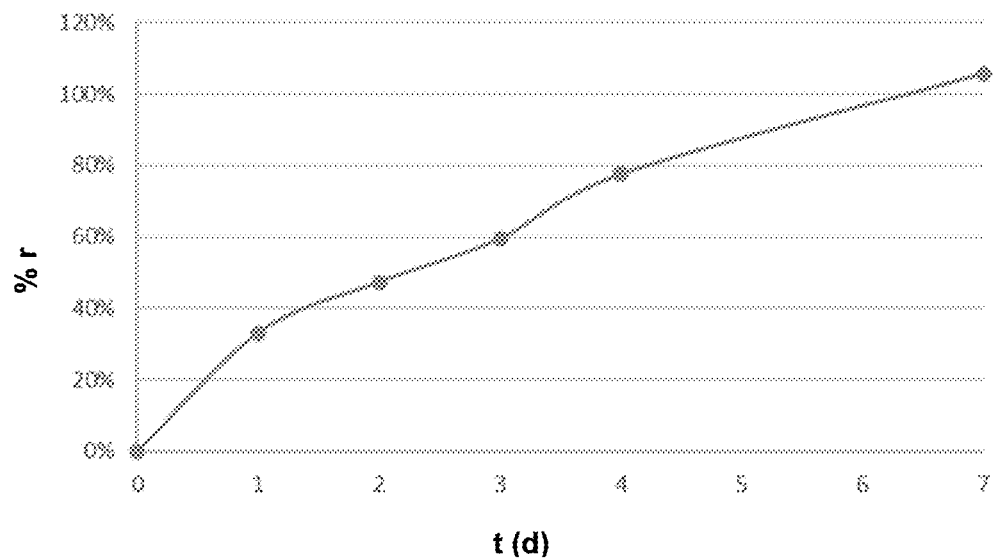
FIG. 9 shows the in vitro release of the active agent (cumulative %) overtime (days) of the beaded membrane of example 1.

FIG. 9 shows the cumulative in vitro release (%) of the beaded membrane of example 1. As can be seen, at 7 days, approximately 100% of the active agent content was released in all cases. The 100% release was confirmed both because the sum of the released material in the different buffer samples was 100%, and because the residual material found in the membrane at the end of the experiment (by dissolving it), at day 7 was zero.

FIG. 10 shows the in vitro release of the active agent (% of the total load) of the beaded membrane showing a shrinkage of about 10% and the non-beaded membrane showing a shrinkage of about 30%. As can be seen, the beaded membrane allows a faster sustained and controlled release of the active agent in comparison to the non-beaded membrane.

CITATION LIST

WO2013144206
US2018000744
Seeram Ramakrishna et al: "Advances in drug delivery via electrospun and electrosprayed nanomaterials", International Journal of Nanomedicine 2013, page 2997
CN105386155
CN107675364
CN106727447

For reasons of completeness, various aspects of the invention are set out in the following numbered clauses:

Clause 1. A beaded nonwoven membrane comprising polymeric nanofibers, and at least one active agent, wherein the nanofibers comprise beads distributed along the nanofiber length and have a mean diameter which is from 1.5 to 20 times the mean diameter of the nanofiber, and wherein the active agent has a water solubility equal to or lower than 33 mg/mL.

Clause 2. The beaded nonwoven membrane according to clause 1, wherein the beads have a mean diameter from 5 to 25 µm.

Clause 3. The beaded nonwoven membrane according to any of the clauses 1-2, wherein the amount of beads is from 500 to 5000 beads/mm$^2$.

Clause 4. The beaded nonwoven membrane according to any of the clauses 1-3, wherein the total content of the active agent is physically entrapped within the membrane but externally arranged to the polymeric nanofibers of the membrane.

Clause 5. The beaded nonwoven membrane according to any of the clauses 1-4, wherein the active agent contained in the nonwoven membrane of the invention is present in the form of particles having an average particle size from 0.1 to 20 µm.

Clause 6. The beaded nonwoven membrane according to any of the clauses 1-5, wherein the amount of therapeutic agent is from 0.01 to 20% by weight with respect to the total weight of the nonwoven membrane.

Clause 7. The beaded nonwoven membrane according to any of the clauses 1-6, which has a degree of linear shrinkage in water at 37° C. and 72 h equal to or lower than 20% when the membrane is contacted with an appropriate amount of medium in which the active agent is solubilized.

Clause 8. The beaded nonwoven membrane according to clause 7, wherein the membrane is capable of releasing an amount equal to or greater than 80% of the total weight of the active agent in a period equal or less than 50% of the degradation time of the polymeric nanofibers after contacting it with an appropriate amount of medium in which the active agent is solubilized.

Clause 9. The beaded nonwoven membrane according to any of the clauses 1-8, wherein the polymeric nanofibers of the membrane have an mean diameter from 50 to 2000 nm.

Clause 10. The beaded nonwoven membrane according to any of the clauses 1-9, wherein the polymeric nanofibers are made of one or more polymers selected from the group consisting of polyglycolic acid (PGA), poly-D,L-lactic acid (PLA), poly-L-lactic acid (PLLA), poly-D,L-lactide-co-glycolide (PLGA), polycaprolactone (PCL), polyethylene glycol (PEG), polydioxanone (PDO), polyvinylalcohol (PVA), collagen, cellulose, hyaluronic acid, polyamide, polyester, polyurethane, polypropylene, elastane, silk, and a combination thereof.

Clause 11. The beaded nonwoven membrane according to clause 10, wherein the polymeric nanofibers are made of one or more polymers selected from the group consisting of polyglycolic acid (PGA), poly-D,L-lactic acid (PLA), poly-L-lactic acid (PLLA), poly-D,L-lactide-co-glycolide (PLGA), polycaprolactone (PCL), polyethylene glycol (PEG), silk, and a combination thereof.

Clause 12. The beaded nonwoven membrane according to any of the clauses 1-11, which comprises at least a first layer comprising polymeric nanofibers, a second layer comprising polymeric nanofibers and at least one active agent, and a third layer comprising polymeric nanofibers.

Clause 13. The beaded nonwoven membrane according to any of the clauses 1-12, wherein the active agent is a therapeutic agent selected from the group consisting of chemotherapeutic agents; nutraceuticals; antibiotics or antifungals; proteins; cells, immunotherapy agents, anti-infectious agents, endocrine agents and cardiovascular agents.

Clause 14. A process for the preparation of the beaded nonwoven membrane as defined in any of the clauses 1-13, which comprises the following steps:
  a) preparing a solution of one or more polymers in a suitable solvent system,
  b) preparing a solution or a suspension of the active agent in a suitable solvent system, wherein the polymer or polymers from step a) are insoluble;
  c) carrying out the electrospinning of the solution from step a) to produce beaded polymeric nanofibers, and, simultaneously, depositing the solution or suspension of step b) over the polymeric nanofibers; and
  d) optionally, drying the nonwoven membrane obtained from step c).

Clause 15. The beaded nonwoven membrane according to anyone of clauses 1-13 for use in the treatment of tumors that include non-resectable areas with vital vessels; in the treatment of surgical borders wherein tumor residues are left; in the treatment of osseous tissues with tumor infiltration or positive bone scan; or in tissue regeneration, wherein the active agent is a chemotherapeutic agent.

The invention claimed is:

1. A beaded nonwoven membrane comprising polymeric nanofibers, and at least one active agent, wherein:
   (a) the nanofibers have a profile characterized by a series of nodulous segments having a bead-shaped morphology spaced from each other and distributed along a length of the nanofibers,
   wherein the segments having the bead-shaped morphology are the segments of the nanofiber having a mean diameter that is 1.5 to 20 times greater than a mean diameter of segments of the nanofibers not having the bead-shaped morphology,
   (b) the active agent has a water solubility equal to or lower than 33 mg/mL, and
   (c) the total content of the active agent is physically entrapped by the membrane by being disposed in spaces between the polymeric nanofibers of the membrane such that no active agent is embedded within the polymeric nanofibers, including the nodulous segments with the bead-shaped morphology.

2. The beaded nonwoven membrane according to claim 1, wherein the segments having the bead-shaped morphology have a mean diameter from 2 to 25 μm.

3. The beaded nonwoven membrane according to claim 1, further comprising a surfactant.

4. The beaded nonwoven membrane according to claim 1, wherein the active agent contained in the nonwoven membrane is present in the form of particles having an average particle size from 0.1 to 20 μm.

5. The beaded nonwoven membrane according to claim 1, wherein an amount of the active agent is from 0.01 to 20% by weight with respect to the total weight of the nonwoven membrane.

6. The beaded nonwoven membrane according to claim 1, wherein the polymeric nanofibers of the membrane have a mean diameter from 50 to 2000 nm.

7. The beaded nonwoven membrane according to claim 1, wherein the polymeric nanofibers are made of one or more polymers selected from the group consisting of polyglycolic acid (PGA), poly-D,L-lactic acid (PDLLA), poly-L-lactic acid (PLLA), poly-D,L-lactide-co-glycolide (PLGA), poly-caprolactone (PCL), polyethylene glycol (PEG), polydioxanone (PDO), polyvinylalcohol (PVA), collagen, cellulose, hyaluronic acid, polyamide, polyester, polyurethane, polypropylene, elastane, and silk.

8. The beaded nonwoven membrane according to claim 7, wherein the polymeric nanofibers are made of one or more polymers selected from the group consisting of polyglycolic acid (PGA), poly-D,L-lactic acid (PDLLA), poly-L-lactic acid (PLLA), poly-D,L-lactide-co-glycolide (PLGA), poly-caprolactone (PCL), polyethylene glycol (PEG), and silk.

9. The beaded nonwoven membrane according to claim 1, which comprises at least a first layer comprising polymeric nanofibers, a second layer comprising polymeric nanofibers and at least one active agent, and a third layer comprising polymeric nanofibers.

10. The beaded nonwoven membrane according to claim 1, wherein the active agent is a therapeutic agent selected from the group consisting of chemotherapeutic agents, nutraceuticals, antibiotics, antifungals, proteins, cells, immunotherapy agents, anti-infectious agents, endocrine agents, and cardiovascular agents.

11. A process for the preparation of the beaded nonwoven membrane as defined in claim 1, which comprises the following steps:
   a) preparing a solution of one or more polymers in a first solvent or a mixture of first solvents;,
   b) preparing a solution or a suspension of the active agent in a second solvent or a mixture of second solvents, wherein the polymer or polymers from step a) are insoluble in the second solvent or the mixture of second solvents;
   c) carrying out an electrospinning process of the solution from step a) to produce polymeric nanofibers having a profile characterized by a series of nodulous segments having a bead-shaped morphology, and, simultaneously, depositing the solution or suspension of step b) over the polymeric nanofibers, wherein the active agent is deposited on the nanofibers once they have been already formed and wherein the depositing the solution or suspension of step b) is carried out by spraying, electrospraying, pouring by gravity, or by a microliter dispenser; and
   d) optionally, drying the nonwoven membrane obtained from step c),
   wherein the total content of the active agent is physically entrapped by the membrane by being disposed in spaces between the polymeric nanofibers of the membrane such that no active agent is embedded within or forms part of the polymeric nanofibers, including the nodulous segments with the bead-shaped morphology.

12. A method for the treatment of tumors located at non-resectable areas with vital vessels, said method comprising the administration in a mammal, including a human, of the beaded nonwoven membrane as defined in claim 1, wherein the active agent is a chemotherapeutic agent.

13. The beaded nonwoven membrane according to claim 2, further comprising a surfactant.

14. The beaded nonwoven membrane according to claim 13, wherein the active agent contained in the nonwoven membrane is present in the form of particles having an average particle size from 0.1 to 20 μm.

15. The beaded nonwoven membrane according to claim 14, wherein an amount of the active agent is from 0.01 to 20% by weight with respect to the total weight of the nonwoven membrane.

16. A method for the treatment of surgical borders where tumor residues are left, said method comprising the administration in a mammal, including a human, of the beaded nonwoven membrane as defined in claim 1, wherein the active agent is a chemotherapeutic agent.

17. A method for the treatment of osseous tissues with tumor infiltration or positive bone scan, said method comprising the administration in a mammal, including a human, of the beaded nonwoven membrane as defined in claim 1, wherein the active agent is a chemotherapeutic agent.

18. A method for tissue regeneration, said method comprising the administration in a mammal, including a human, of the beaded nonwoven membrane as defined in claim 1, wherein the active agent is a chemotherapeutic agent.

19. The beaded nonwoven membrane according to claim 1, wherein the number of nodulous segments having the bead-shaped morphology in the membrane is from 500 to 5000 per $mm^2$ of the membrane.

* * * * *